(12) United States Patent
Gajda et al.

(10) Patent No.: US 10,336,690 B2
(45) Date of Patent: Jul. 2, 2019

(54) METHODS AND SYSTEMS FOR PROCESSING AN ACETONITRILE WASTE STREAM

(71) Applicant: Honeywell International Inc., Morristown, NJ (US)

(72) Inventors: Gregory J. Gajda, Mt. Prospect, IL (US); Mark G. Riley, Hinsdale, IL (US); Venkatraman Mohan, Muskegon, MI (US); Sandra M. Lorenz, Grand Haven, MI (US); Alan P. Cohen, Palatine, IL (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 184 days.

(21) Appl. No.: 14/608,911

(22) Filed: Jan. 29, 2015

(65) Prior Publication Data

US 2015/0239828 A1    Aug. 27, 2015

Related U.S. Application Data (60) Provisional application No. 61/943,701, filed on Feb. 24, 2014, provisional application No. 62/063,281, filed on Oct. 13, 2014.

(51) Int. Cl.
| | |
|---|---|
| *B01D 3/14* | (2006.01) |
| *C07H 1/00* | (2006.01) |
| *B01D 15/26* | (2006.01) |
| *B01D 15/36* | (2006.01) |
| *C07H 21/00* | (2006.01) |
| *C07C 253/34* | (2006.01) |
| *C07C 255/03* | (2006.01) |

(52) U.S. Cl.
CPC .......... *C07C 253/34* (2013.01); *B01D 3/143* (2013.01); *B01D 15/26* (2013.01); *B01D 15/362* (2013.01); *B01D 15/363* (2013.01); *C07H 1/00* (2013.01); *C07H 21/00* (2013.01)

(58) Field of Classification Search
CPC ........ C07H 1/00; C07H 21/00; C07C 253/34; C07C 255/04; B01D 15/362; B01D 15/26; B01D 15/363; B01D 3/143
See application file for complete search history.

(56) References Cited

U.S. PATENT DOCUMENTS

| | | |
|---|---|---|
| 5,440,068 A | 8/1995 | Blackman et al. |
| 5,629,443 A | 5/1997 | Nakamura et al. |
| 5,969,175 A | 10/1999 | Murao et al. |
| 6,326,508 B1 | 12/2001 | Godbole et al. |
| 6,395,142 B1 * | 5/2002 | Miles ............... B01D 3/146 203/74 |
| 6,508,917 B1 * | 1/2003 | Miles ............... B01D 3/146 203/74 |
| 6,780,289 B2 | 8/2004 | Godbole |
| 6,843,890 B1 | 1/2005 | Godbole |
| 7,491,838 B2 | 2/2009 | Cesa et al. |

FOREIGN PATENT DOCUMENTS

| | | |
|---|---|---|
| CN | 100341849 C | 10/2007 |
| EP | 890572 B1 | 10/2001 |
| EP | 1882682 A1 | 1/2008 |
| FR | 2705342 A1 | 11/1994 |
| GB | 2138807 A | 10/1984 |
| GB | 2249308 A | 5/1992 |
| JP | 11035542 A | 2/1999 |
| JP | 2000128847 A | 5/2000 |
| JP | 03175872 B2 | 6/2001 |
| JP | 04637923 B2 | 2/2011 |
| JP | 2011046719 A | 3/2011 |
| WO | 0127120 A2 | 4/2001 |
| WO | 0206212 A2 | 1/2002 |
| WO | 2006121081 A1 | 11/2006 |
| WO | 2013146609 A1 | 10/2013 |

OTHER PUBLICATIONS

The International Search Report dated May 12, 2015 in International Application No. PCT/US2015/015551.
Cui et al., Separation of Acetonitrile-Water by Saline Extractive Distillation, Petrochemical Technology, v 36, n. 12, p. 1229-1233, Dec. 15, 2007; Language: Chinese; ISSN: 10008144; Publisher: Beijing Research Institute of Chemical Industry.
Wang et al., Sugaring-Out Separation of Acetonitrile From Its Aqueous Solution, Chemical Engineering and Technology, v 31, n. 12, p. 1869-1874, Dec. 2008; ISSN: 09307516; Publisher: Wiley-VCH Verlag.
Cori et al., Purification of Acetonitrile From Allyl Alcohol by Distillation, Chim. Ind. (Milan), v 64, n. 1, p. 3-7, Jan. 1982.
Sherman et al., Purification of Acetonitrile for Voltammetry, Anal. Chem. v 40, n. 7, p. 1174-1175, Jun. 1968.
Sevryugova et al., Purification of Acrylonitrile by Fractionation to Remove Acetonitrile, Khim. Prom., v 43, n. 10, p. 776-779, Oct. 1967.
Database WPI, Week 200507, Thomson Scientific London, GB; AN 2005-060618 & JP 2004 339112A (Mitsubishi Rayon Co Ltd) Dec. 2, 2004.

(Continued)

*Primary Examiner* — Lawrence E Crane (74) *Attorney, Agent, or Firm* — Lorenz & Kopf, LLP (57) ABSTRACT

Methods for purifying an acetonitrile waste stream are provided. An exemplary method for purifying an acetonitrile waste stream includes generating an acetonitrile waste stream during oligonucleotide synthesis and fractionating the acetonitrile waste stream to produce a single overhead fraction. The method includes condensing the single overhead fraction to produce a condensed single overhead fraction and contacting the condensed single overhead fraction with an adsorbent material to produce an acetonitrile stream that comprises an amount of an impurity that is reduced relative to the acetonitrile waste stream.

12 Claims, 2 Drawing Sheets

(56) References Cited

OTHER PUBLICATIONS

Extended EP Search Report for Application No. 15751403.5 dated Aug. 25, 2017.

* cited by examiner

METHODS AND SYSTEMS FOR PROCESSING AN ACETONITRILE WASTE STREAM

CROSS-REFERENCE TO RELATED APPLICATIONS

This application claims benefit of provisional application Ser. No. 61/943,701, filed on Feb. 24, 2014, and claims benefit of provisional application Ser. No. 62/063,281, filed on Oct. 13, 2014.

TECHNICAL FIELD

The technical field generally relates to methods and systems for purifying an acetonitrile waste stream and methods for synthesizing oligonucleotides using purified acetonitrile waste streams. More particularly, the technical field relates to methods and systems for purifying an acetonitrile waste stream utilizing fractionation followed by contact with one or more adsorbents.

BACKGROUND

Numerous chemical processes utilize acetonitrile as a solvent or wash, resulting in generation of low grade acetonitrile waste streams. When these processes are conducted on a manufacturing scale, the volume of low grade acetonitrile waste stream produced can be substantial. For example, oligonucleotide (DNA and RNA) synthesis is generally conducted via a four step cycle (deblocking, activation/coupling, capping, and oxidation/sulfurization), which is repeated for each nucleotide added until the desired sequence is obtained. Between each step, oligonucleotides bound to a support are washed with acetonitrile to reduce residual reagents from the prior step. This leads to generation of a tremendous volume of acetonitrile waste stream, with on the order of 2,000 metric tons of acetonitrile required to manufacture approximately 1 metric ton of an oligonucleotide-based active pharmaceutical ingredient (API).

Synthetic oligonucleotide sequences are showing promise for therapeutic, diagnostic, and drug target validation applications in the bio-pharmaceutical industry, and the number of oligonucleotide-based drugs currently in pre-clinical or clinical trials is ever increasing. However, oligonucleotide-based API manufacturers are faced with the expense and difficulty of managing this large volume of acetonitrile waste stream. As such, there is an acute need in the industry for methods and systems to reclaim and purify acetonitrile waste streams to generate purified acetonitrile suitable for reuse. Furthermore, other desirable features and characteristics will become apparent from the subsequent detailed description and the appended claims, taken in conjunction with the accompanying drawings and this background.

BRIEF SUMMARY

Methods and systems for purifying an acetonitrile waste stream and methods for synthesizing an oligonucleotide using a purified acetonitrile waste stream are provided. An exemplary method for purifying an acetonitrile waste stream includes providing an acetonitrile waste stream and fractionating the acetonitrile waste stream to produce a single overhead fraction. The method includes condensing the single overhead fraction to produce a condensed single overhead fraction and contacting the condensed single overhead fraction with an adsorbent to produce an acetonitrile stream that comprises an amount of at least one impurity that is reduced relative to the acetonitrile waste stream.

Other embodiments include methods for synthesizing oligonucleotides. An exemplary method for synthesizing an oligonucleotide includes producing an acetonitrile stream. The acetonitrile stream is produced by providing an acetonitrile waste stream; fractionating the acetonitrile waste stream to produce a single overhead fraction; condensing the single overhead fraction to produce a condensed single overhead fraction; and contacting the condensed single overhead fraction with an adsorbent to produce the acetonitrile stream comprising an amount of at least one impurity that is reduced relative to the acetonitrile waste stream. The method for synthesizing an oligonucleotide further includes washing a nucleotide or nucleotide bound support with a volume of the acetonitrile stream.

Also provided herein are systems for purifying an acetonitrile waste stream. An exemplary system includes a fractionation zone configured to receive an acetonitrile waste stream and produce an overhead fraction. The system further includes an adsorbent zone configured to contain an adsorbent selected from the group consisting of an adsorbent that reduces an amount of organic and/or inorganic iodine-containing species, an adsorbent that reduces an amount of organic and/or inorganic sulfur-containing species, an adsorbent that reduces an amount of water, and an adsorbent that reduces an amount of basic nitrogen-containing compounds, wherein the adsorbent zone is further configured to sequentially receive and contact the overhead fraction with the adsorbent contained therein.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Methods and systems for purifying an acetonitrile waste stream are described herein. In the following description, specific details are set forth with respect to purifying an acetonitrile waste stream generated during oligonucleotide synthesis. It will be understood by one of skill in the art that these specific details need not necessarily be employed to practice embodiments herein and that application of the methods and systems described herein need not be limited to acetonitrile waste streams generated during oligonucleotide synthesis. As will be appreciated, the acetonitrile purification methods and systems provided herein may be used to purify acetonitrile from a variety of waste sources, including but not limited to waste streams resulting from a single wash step or pooled wash steps from oligonucleotide synthesis, high performance liquid chromatography waste, waste from pharmaceutical manufacturing, etc. Further, in some instances, well known processes, apparatus, materials, etc., may not be described in full detail. However, such well known processes, apparatus, materials, etc. will be understood by one of skill in the art.

As used herein the terms "purifying" and variants thereof refer to the reduction of the amount of one or more impurities in a composition. As a general concept, purification may be accomplished via any number of techniques known in the art, depending on the nature of the composition to be purified and impurity to be reduced. Purification does not necessarily result in a pure product, completely absent of all impurities or of any particular impurity.

Figure 1:
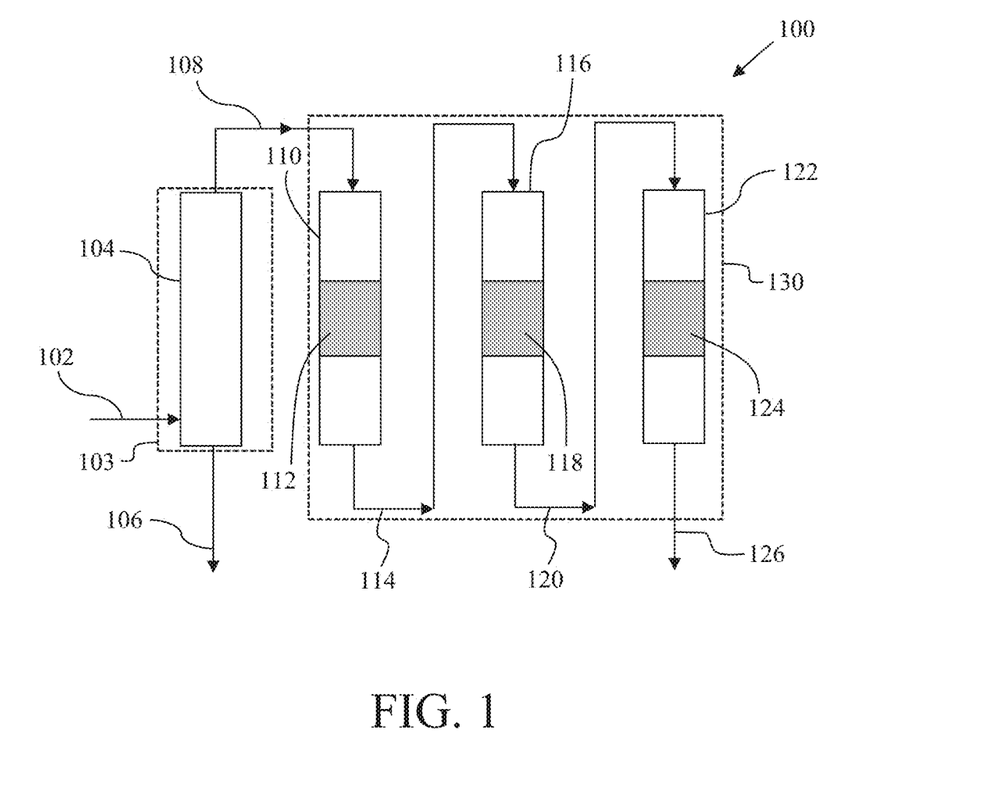
FIG. 1 is a schematic illustration of a system and method for purifying an acetonitrile waste stream in accordance with an exemplary embodiment.

Some of the methods and systems described herein utilize a plurality of purification steps, including fractionation of an acetonitrile waste stream. In some embodiments, fractionation is an initial purification step. Referring to FIG. 1, in an exemplary embodiment, fractionation of an acetonitrile waste stream 102 is conducted using a system 100 having a fractionation zone 103 including a distillation or fractionation column 104. In specific embodiments, the fractionation column 104 contains internals such as packing, trays, sieves, bubble caps or similar mechanical configurations that can provide stages of multiple, step wise contact for vapor-liquid streams flowing through the column The number of stages and types of internals will vary depending on the specific composition of the acetonitrile waste stream, inlet location, reflux ratios, desired column efficiency, etc. As such, the internal profile of fractionation column 104 may vary from one application to another.

The acetonitrile waste stream 102 may come from various sources and contain some impurities with boiling points above and some impurities with boiling points below that of acetonitrile. In this regard, some acetonitrile purification methods rely on taking a "heart cut" of the distillate. For instance, some methods use two fractionation columns: the first fractionation column to separate acetonitrile and lower boiling impurities (in a first overhead fraction) from higher boiling impurities (in a first bottoms fraction), and the second fractionation column to separate acetonitrile (in a second bottoms fraction) from the lower boiling impurities (in a second overhead fraction).

Advantageously, methods and systems described herein do not require such a complex fractionation scheme. Rather, in some embodiments, the fractionation zone 103 includes a single column 104 and a single overhead fraction 108 is collected up to a single cut point, e.g., just above the boiling point of acetonitrile (such as about 81° C. or 82° C. at standard pressure (1 ATM)). As used herein, the term "overhead" fraction means a fraction removed from an upper portion of a fractionation column The overhead fraction includes components of the original mixture with lower boiling points than components found in the "bottoms" (i.e., a fraction that remains at and/or is removed from a lower portion of the fractionation column). This single overhead fraction 108 comprises acetonitrile and lower temperature boiling impurities. In some embodiments, the single overhead fraction 108 may also comprise some higher boiling impurities, such as toluene, due to azeotropic behavior. Methods and systems described herein accomplish further purification of the overhead fraction 108 by condensing the overhead fraction 108 and contacting the condensed overhead fraction 108 with one or more adsorbents (e.g., adsorbents 112, 118, and 124 contained within columns 110, 116, and 122, respectively). The nature of specific adsorbents used in the subsequent purification steps is determined by the identity and levels of impurities which remain in the overhead fraction, and thus is impacted by the source of the acetonitrile waste stream.

As discussed above, numerous scientific and manufacturing processes utilize acetonitrile streams as a solvent or as a wash solution, and thus generate an acetonitrile waste stream. Various processes require differing degrees of purity of the acetonitrile stream, and/or may require certain degrees of purity with respect to one or more particular impurities. One such process that generates a particularly large volume of acetonitrile waste is the manufacture of synthetic oligonucleotides (DNA and RNA). Oligonucleotide synthesis is generally conducted via a four step cycle (deblocking, activation/coupling, capping, and oxidation/sulfurization) with an acetonitrile wash between each cycle. As each step in a cycle uses different reagents, the acetonitrile waste stream generated from washing after each step is likely contaminated with different types and levels of impurities.

For instance, each oligonucleotide synthesis cycle typically begins with a blocked nucleotide covalently linked to a support. The blocked nucleotide is deblocked in a first step, typically via reaction with an amount of dichloroacetic acid in the presence of toluene or dichloromethane. Once the deblocking reaction is complete, the reagents are drained, and the deblocked oligonucleotides (attached to a support) are washed with acetonitrile Impurities found in the resulting acetonitrile waste stream may include unreacted reagents, residual solvent, and/or byproducts of the deblocking reaction. For instance, impurities in the deblocking acetonitrile waste stream may include toluene, acetic acid, trichloromethane, and/or propanenitrile Impurities in the deblocking acetonitrile waste stream typically constitute 15-30 wt. %. In an exemplary embodiment, the acetonitrile waste stream 102 includes acetonitrile waste generated during an acetonitrile washing step after a deblocking step of an oligonucleotide synthesis.

The second step in the oligonucleotide synthesis cycle involves activating and coupling the deblocked oligonucleotides. Activation is carried out via contact with any suitable activator as known in the art. After activation, the deblocked oligonucleotides are coupled, i.e., reacted, with a phosphoramidite to form a phosphite oligomer. Phosphoramidites are variously selected from among all available phosphoramidites, with the reactions proceeding as known in the art. After coupling, the reagents are drained and the oligonucleotides are washed with acetonitrile. Again, impurities found in the resulting acetonitrile waste stream may include unreacted reagents, residual solvent, or byproducts of the activation and coupling reactions. For instance, impurities in the activation/coupling acetonitrile waste stream may include pyridine, propanenitrile, and/or toluene Impurities in the coupling acetonitrile waste stream again typically constitute 15-30 wt. %. In an exemplary embodiment, the acetonitrile waste stream 102 includes acetonitrile waste generated during an acetonitrile washing step after an activation/coupling step of an oligonucleotide synthesis.

Typically, during the coupling step, only a portion of the deblocked nucleotides react with the phosphoramidite, and any unreacted nucleotides must be capped. Capping is carried out by contacting the unreacted nucleotides with an amount of acetic anhydride and an amount of N-methylimidazole. After coupling, these reagents are drained and the oligonucleotides are again washed with acetonitrile. Again, impurities found in the resulting acetonitrile waste stream may include unreacted reagents, residual solvent, or byproducts of the capping reaction. For instance, impurities in the capping acetonitrile waste stream may include N-methylimidazole, acetic acid, acetic anhydride, lutidine, pyridine, tetrahydrofuran, propanenitrile, and/or toluene. Impurities in the capping acetonitrile waste stream again typically constitute 15-30 wt. %. In an exemplary embodiment, the acetonitrile waste stream 102 includes acetonitrile waste generated during an acetonitrile washing step after a capping step of an oligonucleotide synthesis.

Finally, phosphite oligomers formed in the activation/coupling step are either oxidized or sulfurized. Oxidation is accomplished, e.g., via reaction with iodine in the presence of water and pyridine. Sulfurization is accomplished, e.g., via reaction with phenyl acetyl disulfide in the presence of acetonitrile and picoline. After oxidation or sulfurization, the reagents are drained and the oligonucleotides are again washed with an acetonitrile wash stream Impurities found in the resulting acetonitrile waste stream may include unreacted reagents, residual solvent, or byproducts of the oxidation or sulfurization reaction. For instance, impurities in an oxidation acetonitrile waste stream may include organic and inorganic iodine, toluene, tetrahydrofuran, pyridine, propanenitrile, and water. Alternatively, impurities in the sulfurization acetonitrile waste stream may include, e.g., pyridine, propanenitrile, and/or toluene Impurities in the oxidation or sulfurization acetonitrile waste stream again typically constitute 15-30 wt. %. In an exemplary embodiment, the acetonitrile waste stream 102 includes acetonitrile waste generated during an acetonitrile washing step after an oxidation and/or sulfurization step of an oligonucleotide synthesis.

As will be appreciated, the type and amounts of impurities found in wash streams from each of the above describe steps will very likely be different. The methods and systems described herein may be used to purify an acetonitrile waste stream from a washing step after any particular step, or may be used to purify a pooled acetonitrile waste stream comprising a plurality of acetonitrile waste streams from the washing steps after any combination of the above described steps.

The identity and amount of impurities in the overhead fraction may vary depending on the source of the acetonitrile waste stream and appropriate adsorbent(s) may be selected on those considerations as well as the final grade (i.e., overall purity) of acetonitrile end product desired. For instance, an overhead fraction obtained by distillation of pooled acetonitrile waste resulting from oligonucleotide synthesis may contain impurities such as water, toluene, and various other impurities depending on whether oxidation was conducted with iodine or sulfur. Waste from an iodine-type synthesis may further comprise organic and/or inorganic iodine-containing species as well as basic nitrogen-containing compounds such as pyridine, as well as various alcohols (e.g., methanol), esters (e.g., methyl ester of acetic acid), nitriles (e.g., propanenitrile), and halogenated hydrocarbons (e.g., trichloromethane). Waste from a sulfur-type synthesis may further comprise organic and/or inorganic sulfur-containing species as well as basic nitrogen-containing compounds (e.g., pyridine), various alcohols (e.g., methanol), esters (e.g., methyl ester of acetic acid), nitriles (e.g., propanenitrile), and halogenated hydrocarbons (e.g., trichloromethane).

As noted above, in an exemplary embodiment, the acetonitrile waste stream 102 passes into fractionation zone 103 to a fractionation column 104 in which the acetonitrile waste stream 102 is separated through a single fractionation step into an overhead fraction 108 containing acetonitrile and lower boiling impurities, and a bottoms fraction 106 containing acetonitrile and higher boiling impurities. In an exemplary embodiment, the single fractionation step is conducted such that at least the majority of acetonitrile originally present in the acetonitrile waste stream 102 is contained within the overhead fraction 108. In some embodiments, the overhead fraction 108 may contain 75% or more, such as 85% or more, such as 95% or more, of the acetonitrile originally contained in the acetonitrile waste stream 102. That is, the overhead fraction 108 may contain about 75% to about 100%, such as about 85% to about 100%, such as about 95% to about 100%, of the acetonitrile originally contained in the acetonitrile waste stream 102. Bottoms fraction 106 is removed from the fractionation column 104 and collected for disposal or other remediation.

In an exemplary embodiment, condensed overhead fraction 108 exits the fractionation zone 103 and is passed to an adsorbent zone 130. In the adsorbent zone 130, the condensed overhead fraction 108 enters a first adsorbent column 110 that is configured to contain a first adsorbent 112. The first overhead fraction 108 is purified by contact with the first adsorbent 112 to generate purified acetonitrile stream 114. A condensed overhead fraction 108 from pooled acetonitrile waste resulting from iodine-based oligonucleotide synthesis may contain unacceptable levels of organic and/or inorganic iodine-containing species and/or unacceptable levels of organic and/or inorganic sulfur-containing species. Thus, in some embodiments, the condensed overhead fraction 108 may be contacted with an adsorbent 112 selected to reduce the amounts of these organic and/or inorganic iodine-containing and/or sulfur-containing species, resulting in a purified acetonitrile stream 114. Suitable adsorbents include silver (Ag)-exchange zeolites. In some embodiments, the Ag-exchange zeolites are Ag-exchange faujasite zeolites, and in particular, faujasite zeolites with a silicon:aluminum (Si:Al) mole ratio of at least about 1.2, such as with a Si:Al mole ratio of at least about 2.0. In some embodiments utilizing Ag-exchange faujasite zeolites, Ag is present at a minimum of about 3 wt. %, such as at least about 15 wt. %. In some specific embodiments, the Ag is partially ion-exchanged and partially precipitated on the zeolite, with the fraction of Ag ion-exchanged depending on the Si:Al mole ratio and wt. % Ag. Typically, however, at least about 10 wt. % of the Ag is ion-exchanged on the zeolite. This is not to say that iodine-reducing adsorbents are limited to faujasite zeolites. Rather, any other suitable zeolite may be used.

In embodiments utilizing one or more Ag-exchange faujasite zeolites to reduce organic and/or inorganic iodine-containing species in the condensed overhead fraction, the adsorbent(s) may be used by contacting the condensed overhead fraction 108 with the adsorbent(s) at a weight ratio of at least about 1:100,000 adsorbent:condensed overhead fraction 108. In some embodiments, the weight ratio is at least about 1:10,000, 1:1000, or 1:100 adsorbent:condensed overhead fraction 108. Contact may be conducted via a batch process or via a continuous process with suitable apparatus, temperatures, pressures, and flow rates.

In some embodiments, the methods provided herein are used to purify an acetonitrile waste stream 102 comprising organic and/or inorganic iodine-containing compounds as impurities. In some embodiments, the resulting purified acetonitrile stream 114 comprises about 25 ppm of iodine or less, such as about 10 ppm of iodine or less, such as about 5 ppm of iodine or less, such as about 1 ppm of iodine or less, such as about 0.5 ppm of iodine or less. In some embodiments, the resulting purified acetonitrile stream 114 comprises about 0.1 ppm to about 25 ppm of iodine, such as about 0.1 ppm to about 10 ppm of iodine, such as about 0.1 ppm to about 5 ppm of iodine, such as about 0.1 ppm to about 1 ppm of iodine, such as about 0.1 ppm to about 0.5 ppm of iodine.

In some embodiments, the methods provided herein are used to purify an acetonitrile waste stream 102 comprising organic and/or inorganic sulfur-containing compounds as impurities. In some embodiments, the resulting purified acetonitrile stream 114 comprises about 10 ppm of sulfur or less, such as about 6 ppm of sulfur or less, such as about 5 ppm of sulfur or less, such as about 4 ppm of sulfur or less. In some embodiments, the resulting purified acetonitrile stream 114 comprises from about 0.5 ppm to about 10 ppm of sulfur, such as from about 0.5 ppm to about 6 ppm of sulfur, such as from about 0.5 ppm to about 5 ppm of sulfur, such as about 0.5 ppm to about 4 ppm of sulfur.

If present, it may be desirable to reduce the amount of basic N-containing compounds, such as pyridine, in the purified acetonitrile stream 114. Thus, in an exemplary embodiment, the purified acetonitrile 114 is passed to a second adsorbent column 116 that is configured to contain a basic N reducing adsorbent 118. Again, a basic N reducing adsorbent may be the only adsorbent used; alternatively, a basic N reducing adsorbent may be one of a plurality of adsorbents used. If a plurality of adsorbents is used, the adsorbents may be used sequentially. In such embodiments, a basic N reducing adsorbent may be used at any position in the sequence.

In the particular exemplary embodiment in FIG. 1, the purified acetonitrile stream 114 is contacted with a basic N reducing adsorbent 118, resulting in purified acetonitrile stream 120 that comprises an amount of basic N-containing compound impurities that is reduced relative to acetonitrile waste stream 102. Purified acetonitrile stream 120 may be collected for use or subjected to further purification as desired.

In some embodiments, a basic N adsorbent may comprise an acidic cation exchange resin. In such embodiments, the relative proportion of adsorbents used per volume of the acetonitrile stream to be purified (e.g., condensed overhead fraction 108 or purified acetonitrile stream 114) may vary depending on the specific adsorbent, amount of basic N-containing impurities contained in the acetonitrile stream, and desired level of basic N-containing impurities in the resulting purified acetonitrile stream. In some embodiments, an acidic cation exchange resin such as Amberlyst™-15 is used to reduce basic N-containing impurities in an acetonitrile stream at a ratio of at least about 1 g adsorbent to 10 L acetonitrile stream, such as at least about 1 g adsorbent to 0.1 L acetonitrile stream.

Thus, in some embodiments the methods provided herein are used to purify an acetonitrile waste stream 102 comprising one or more basic N-containing compounds as impurities. In some embodiments, a purified acetonitrile stream 120 is generated by removing such impurities from an acetonitrile stream such that the resulting purified acetonitrile stream comprises about 100 ppm of basic N-containing compounds or less, such as about 50 ppm of basic N-containing compounds or less, such as about 25 ppm of basic N-containing compounds or less, such as about 10 ppm of basic N-containing compounds or less. In some embodiments, a purified acetonitrile stream 120 is generated by removing such impurities from an acetonitrile stream such that the resulting purified acetonitrile stream comprises from about 1 ppm to about 100 ppm of basic N-containing compounds, such as from about 1 ppm to about 50 ppm of basic N-containing compounds, such as from about 1 ppm to about 25 ppm of basic N-containing compounds, such as from about 1 ppm to about 10 ppm of basic N-containing compounds.

In some embodiments, an acid exchange resin may also reduce the amount of cations present in the purified acetonitrile stream 114. For example, impurities such as cationic Fe, Mg, Cr, Ni, Ag, and $I_2$, may be reduced by contact with a cation exchange resin. In some embodiments, cation reduction occurs concurrently with basic N reduction via contact with a basic N reducing adsorbent comprising an acidic cation exchange resin as described above. In some embodiments, the purified acetonitrile 120 comprises less than about 5 ppm cationic Fe, such as from about 0.1 ppm to about 5 ppm, as an impurity. In some embodiments, the purified acetonitrile 120 comprises less than about 5 ppm cationic Mg, such as from about 0.1 ppm to about 5 ppm, as an impurity. In some embodiments, the purified acetonitrile 120 comprises less than about 5 ppm cationic Cr, such as from about 0.1 ppm to about 5 ppm, as an impurity. In some embodiments, the purified acetonitrile 120 comprises less than about 5 ppm cationic Ni, such as from about 0.1 ppm to about 5 ppm, as an impurity. In some embodiments, the purified acetonitrile 120 comprises less than about 5 ppm cationic Ag, such as from about 0.1 ppm to about 5 ppm, as an impurity. In some embodiments, the purified acetonitrile 120 comprises less than about 5 ppm iodine/iodide, such as from about 0.1 ppm to about 5 ppm, as an impurity.

It may be desirable to reduce the amount of water present in the condensed purified acetonitrile 120. In some embodiments, including the example shown in FIG. 1, the purified acetonitrile 120 passes to a third adsorbent column 122. In these embodiments, the third adsorbent column 122 is configured to contain a water-reducing adsorbent (i.e., a desiccant) 124. The purified acetonitrile 120 is contacted with the water reducing adsorbent 124 to produce a purified acetonitrile 126 that exits the adsorption zone 130.

In some embodiments, potassium (K)-exchanged Linde Type A (LTA)-type molecular sieves bound with an inorganic binder may be used as a water removal adsorbent 124. It has surprisingly been found that porous desiccants exhibit increased performance (i.e., higher water adsorption capacity) for reduction of water in acetonitrile waste streams if they have been treated to partially close their pore structure. Thus, in some embodiments, one or more porous desiccants (including one or more K-exchanged LTA-type molecular sieves bound with inorganic binders) may be treated by any suitable process as known in the art to partially close the pores of the desiccant prior to use. However, care must be taken not to close the pores too much and thus restrict water adsorption capacity. The degree of pore closure may be measured by determining the smallest molecule that will not adsorb more than 1 wt. % of the molecule when exposed at one atmosphere partial pressure, also known as a plug-gauge molecule. In some embodiments, the desiccant is an LTA-type adsorbent that has been treated with steam to partially close the desiccant's pore structure to the point that the desiccant has a limited ability to adsorb ethylene, difluoromethane, or both.

In embodiments utilizing one or more LTA-type adsorbents to reduce water in a purified acetonitrile 120 from pooled acetonitrile waste from oligonucleotide synthesis, the adsorbent(s) may be used at a weight ratio of at least 5-10 mg desiccant per gram of acetonitrile to be purified. In some embodiments, one or more LTA-type adsorbents are used with a minimum water adsorption capacity of 10 wt. %.

Contact may be conducted via a batch or a continuous process, with suitable apparatus, temperatures, pressures, and flow rates.

In some embodiments, reducing the amount of water present in the condensed purified acetonitrile 120 is conducted via a liquid phase process. In these embodiments, the purified acetonitrile 120 is in a liquid phase when it is contacted with the water-reducing adsorbent 124.

In the alternative or in addition, reducing the amount of water present in a purified acetonitrile may be conducted via a vapor phase process, such as vapor phase pressure-swing adsorption (PSA). In an exemplary embodiment, a purified acetonitrile leaving a fractionation column may be processed so as to reduce or eliminate condensation of the overhead fraction. Rather, a purified acetonitrile leaving a fractionation column is further heated, e.g., superheated by about 25° C. above the fractionation temperature, and the heated vapor is fed to a column containing a water-reducing adsorbent. In some embodiments, the water-reducing adsorbent is a potassium (K)-exchanged Linde Type A (LTA)-type molecular sieves bound with an inorganic binder, as described above, which may or may not have partially closed pores. After contact with the water-reducing adsorbent, the vapor is directed to a heat exchanger where it is condensed into a liquid phase purified acetonitrile. This liquid phase purified acetonitrile may be subjected to further purification, including via contact with other adsorbent materials as described herein, as desired. It will be appreciated by those of skill in the art that a plurality of columns containing water-reducing adsorbents may be utilized in parallel in the methods described herein such that after saturation of the adsorbent in a first column, the acetonitrile vapor to be dried may be directed to a second column, while the adsorbent in the first column is regenerated. In some embodiments, regeneration conditions include stripping water from an adsorbent by reducing the pressure and condensing the released materials as a liquid waste stream. In some embodiments, at least a portion of the liquid waste stream may be redirected back to the fractionation column for further processing. In some embodiments, the average water delta load (i.e., the change in average water content of the adsorbent from the beginning to the end of an adsorption step) is about 1 to about 3 kg of water per 100 kg of adsorbent. In these embodiments, the adsorption conditions, such as pressure, feed rate, and flow rate, may be such that an adsorption step may take from about 5 to about 10 minutes.

Thus, in some embodiments the methods provided herein are used to purify an acetonitrile waste stream 102 comprising water as an impurity. In some related embodiments, the acetonitrile waste stream 102 is fractionated and the overhead fraction is contacted with a desiccant with a partially closed pore structure. In some embodiments, the purified acetonitrile 126 that has been purified by contact with a desiccant comprises about 2000 ppm of water or less, such as about 1000 ppm of water or less, such as about 500 ppm of water or less, such as about 150 ppm of water or less, 100 ppm of water or less, such as about 50 ppm of water or less, such as about 25 ppm of water or less.

While the various embodiments above describe the acetonitrile waste stream passing from a fractionation column, then sequentially through an iodine-reducing adsorbent, through a basic N-containing compound-reducing adsorbent, and through a water-reducing adsorbent, it will be appreciated that the scope herein is not so limited. Rather, it will be understood that only one or two of the adsorbents can be used in addition to the fractionation column and/or that the adsorbents can be used in a different order, without limit. For example, after fractionation and condensation, the condensed overhead fraction 108 can be contacted with the basic N-containing compound-reducing adsorbent and the resulting acetonitrile stream contacted with the water-reducing adsorbent, or the condensed overhead fraction 108 can be contacted with a water-reducing adsorbent and the resulting stream contacted with the iodine-reducing adsorbent.

In some embodiments, the methods provided herein are used to purify an acetonitrile waste stream 102 from oligonucleotide synthesis to generate a purified acetonitrile 126 suitable for reuse in various industrial or manufacturing processes. In some embodiments, the purified acetonitrile 126 is suitable for reuse as a between-step wash solution in an oligonucleotide synthesis conducted with between-step acetonitrile washes. In some embodiments, the purified acetonitrile 126 is greater than about 85% pure, such as greater than or equal to about 95% pure, as determined by gas chromatography.

Figure 2:
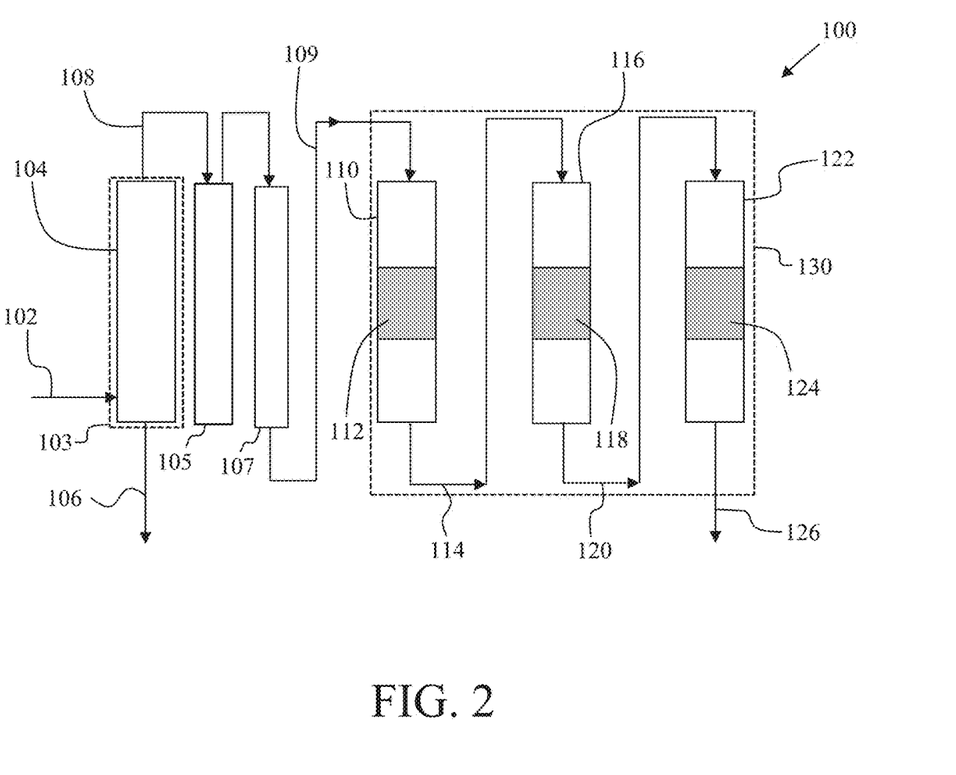
FIG. 2 is a schematic illustration of a system and method for purifying an acetonitrile waste stream in accordance with another exemplary embodiment.

Referring now to FIG. 2, in another exemplary embodiment, processing of an acetonitrile waste stream 102 is again conducted using a system 100 having a fractionation zone 103 including a distillation or fractionation column 104. In an exemplary embodiment, the waste stream 102 and components and streams of the system 100 in FIG. 2 are as described above in relation to FIG. 1.

As shown in FIG. 2, the acetonitrile waste stream 102 passes into fractionation zone 103 and to a fractionation column 104 in which the acetonitrile waste stream 102 is separated through a single fractionation step into an overhead fraction 108 containing acetonitrile and lower boiling impurities, and a bottoms fraction 106 containing acetonitrile and higher boiling impurities. As noted above, the single fractionation step is conducted such that at least the majority of acetonitrile originally present in the acetonitrile waste stream 102 is contained within the overhead fraction 108. In some embodiments, the overhead fraction 108 may contain 75% or more, such as 85% or more, such as 95% or more, of the acetonitrile originally contained in the acetonitrile waste stream 102. That is, the overhead fraction 108 may contain about 75% to about 100%, such as about 85% to about 100%, such as about 95% to about 100%, of the acetonitrile originally contained in the acetonitrile waste stream 102. Bottoms fraction 106 is removed from the fractionation column 104 and collected for disposal or other remediation.

In FIG. 2, the step of condensing overhead fraction 108 is expressly illustrated as being conducted in condensation zone 107. In such embodiments, any conventional means or system configuration for condensation may be utilized. As shown, the overhead fraction 108 exits the fractionation zone 103 and enters condensation zone 107.

Alternative or additionally, reducing the amount of water present in a acetonitrile stream may be conducted via a vapor phase process, such as vapor phase pressure-swing adsorption (PSA). In an exemplary embodiment, upon leaving the fractionation column 104, an overhead fraction 108 may be processed so as to reduce or eliminate condensation of the overhead fraction 108. In these embodiments, the overhead fraction 108 may be further heated, e.g., superheated by about 25° C. above the fractionation temperature, and the heated vapor fed to a column containing a water-reducing adsorbent. This heating and water reduction is conducted in an optional vapor-phase water reduction zone 105, as seen in FIG. 2. In some embodiments, the water-reducing adsorbent is a potassium (K)-exchanged Linde Type A (LTA)-type molecular sieves bound with an inorganic binder, as described below, which may or may not have partially closed pores. After contact with the water-reducing adsorbent, the vapor is directed to condensation zone 107 (e.g., a heat exchanger) where it is condensed into a liquid phase or condensed acetonitrile stream 109. This condensed acetonitrile stream 109 may be subjected to further purification, including via contact with other adsorbent materials as described herein, as desired.

It will be appreciated by those of skill in the art that a plurality of columns containing water-reducing adsorbents may be utilized in parallel in the methods described herein such that after saturation of the adsorbent in a first column, the acetonitrile vapor to be dried may be directed to a second column, while the adsorbent in the first column is regenerated. In some embodiments, regeneration conditions include stripping water from an adsorbent by reducing the pressure and condensing the released materials as a liquid waste stream. In some embodiments, at least a portion of the liquid waste stream may be redirected back to the fractionation column for further processing. In some embodiments, the average water delta load (i.e., the change in average water content of the adsorbent from the beginning to the end of an adsorption step) is about 1 to about 3 kg of water per 100 kg of adsorbent. In these embodiments, the adsorption conditions, such as pressure, feed rate, and flow rate, may be such that an adsorption step may take from about 5 to about 10 minutes.

As shown, condensed overhead fraction 109 is passed to adsorption zone 130 where the condensed overhead fraction 109 enters a first adsorbent column 110 that is configured to contain a first adsorbent 112. The condensed overhead fraction 109 is purified by contact with the first adsorbent 112 to generate purified acetonitrile stream 114. The condensed overhead fraction 109 from pooled acetonitrile waste resulting from iodine-based oligonucleotide synthesis may contain unacceptable levels of organic and/or inorganic iodine-containing species. Similarly, the condensed overhead fraction 109 from pooled acetonitrile waste resulting from sulfur-based oligonucleotide synthesis may contain unacceptable levels of organic and/or inorganic sulfur-containing species. Thus, in some embodiments, the condensed overhead fraction 109 may be contacted with an adsorbent 112 selected to reduce the amounts of these organic and/or inorganic iodine-containing and/or sulfur-containing species, resulting in a purified acetonitrile stream 114. Suitable adsorbents include silver (Ag)-exchange zeolites. In some embodiments, the Ag-exchange zeolites are Ag-exchange faujasite zeolites, and in particular, faujasite zeolites with a silicon:aluminum (Si:Al) mole ratio of at least about 1.2, such as with a Si:Al mole ratio of at least about 2.0. In some embodiments utilizing Ag-exchange faujasite zeolites, Ag is present at a minimum of about 3 wt. %, such as at least about 15 wt. %. In some specific embodiments, the Ag is partially ion-exchanged and partially precipitated on the zeolite, with the fraction of Ag ion-exchanged depending on the Si:Al mole ratio and wt. % Ag. Typically, however, at least about 10 wt. % of the Ag is ion-exchanged on the zeolite. This is not to say that iodine-reducing adsorbents are limited to faujasite zeolites. Rather, any other suitable zeolite may be used.

In embodiments utilizing one or more Ag-exchange faujasite zeolites to reduce organic and/or inorganic iodine-containing species in the condensed overhead fraction 109, the adsorbent(s) may be used by contacting the condensed overhead fraction 109 with the adsorbent(s) at a weight ratio of at least about 1:100,000 adsorbent:condensed overhead fraction 109. In some embodiments, the weight ratio is at least about 1:10,000, 1:1000, or 1:100 adsorbent:condensed overhead fraction 109. Contact may be conducted via a batch process or via a continuous process with suitable apparatus, temperatures, pressures, and flow rates.

In some embodiments, the methods provided herein are used to purify an acetonitrile waste stream 102 comprising organic and/or inorganic iodine-containing compounds as impurities. In some embodiments, the resulting purified acetonitrile stream 114 comprises about 25 ppm of iodine or less, such as about 10 ppm of iodine or less, such as about 5 ppm of iodine or less, such as about 1 ppm of iodine or less, such as about 0.5 ppm of iodine or less. In some embodiments, the resulting purified acetonitrile stream 114 comprises from about 0.1 ppm to about 25 ppm of iodine, such as from about 0.1 ppm to about 10 ppm of iodine, such as from about 0.1 ppm to about 5 ppm of iodine, such as from about 0.1 ppm to about 1 ppm of iodine, such as from about 0.1 ppm to about 0.5 ppm of iodine.

In some embodiments, the methods provided herein are used to purify an acetonitrile waste stream 102 comprising organic and/or inorganic sulfur-containing compounds as impurities. In some embodiments, the resulting purified acetonitrile stream 114 comprises about 10 ppm of sulfur or less, such as about 6 ppm of sulfur or less, such as about 5 ppm of sulfur or less, such as about 4 ppm of sulfur or less. In some embodiments, the resulting purified acetonitrile stream 114 comprises from about 0.5 ppm to about 10 ppm of sulfur, such as from about 0.5 ppm to about 6 ppm of sulfur, such as from about 0.5 ppm to about 5 ppm of sulfur, such as from about 0.5 ppm to about 4 ppm of sulfur.

It has further been found that a basic anion exchange resin, such as Amberlyst™ A26 from Rohm and Haas Co., may be used to reduce an amount of organic and/or inorganic sulfur-containing compounds in an acetonitrile waste stream 102 comprising such impurities. A basic anion exchange resin may be the only adsorbent used; alternatively, a basic anion exchange resin may be one of a plurality of adsorbents used. If a plurality of adsorbents is used, the adsorbents may be used sequentially. In such embodiments, a basic anion exchange resin may be used at any position in the sequence.

In embodiments where a basic anion exchange resin is used, the relative proportion of adsorbents used per volume of the overhead fraction may vary depending on the specific adsorbent and level of sulfur-containing impurities. In some embodiments, a basic anion exchange resin such as Amberlyst™ A26 is used to reduce sulfur-containing impurities in the condensed overhead fraction 109 at a ratio of at least about 1 g adsorbent to 10 L condensed overhead fraction 109, such as at least about 1 g adsorbent to 1 L condensed overhead fraction 109. In some embodiments, the resulting purified acetonitrile stream 114 comprises about 10 ppm of sulfur or less, such as about 6 ppm of sulfur or less, such as about 5 ppm of sulfur or less, such as about 4 ppm of sulfur or less, such as about 1 ppm or less of sulfur. In some embodiments, the resulting purified acetonitrile stream 114 comprises from about 0.5 ppm to about 10 ppm of sulfur, such as from about 0.5 ppm to about 6 ppm of sulfur, such as from about 0.5 ppm to about 5 ppm of sulfur, such as from about 0.5 ppm to about 4 ppm of sulfur, such as from about 0.5 ppm to about 1 ppm of sulfur.

Certain basic anion exchange resins may be sufficiently strong bases to catalyze the hydrolysis of acetonitrile if water is present. As the acetonitrile waste stream 102 typically comprises water as a significant impurity, some embodiments where purified acetonitrile stream 114 results from contact with a basic anion exchange resin may further contact purified acetonitrile stream 114 with an acid cation exchange resin, such as Amberlyst™-15 from Rohm and Haas Co. In such embodiments, the acid cation exchange resin prevents formation of acetamide via hydrolysis of acetonitrile, or adsorbs significantly all acetamide that does form. In some embodiments where an acid cation exchange resin is used in combination with a basic anion exchange resin, both resins may be combined in an adsorbent resin mix for contact with acetonitrile waste stream 102 (or a fraction thereof, e.g., condensed overhead fraction 109) to be purified. In these embodiments, the ratio of basic anion exchange resin to acidic cation exchange resin in an adsorbent resin mix is about 1:0.5 to about 1:1.5, such as about 1:1.

If present, it may be desirable to reduce the amount of basic N-containing compounds, such as pyridine, in the purified acetonitrile stream 114. Thus, in an exemplary embodiment, the purified acetonitrile 114 is passed to a second adsorbent column 116 that is configured to contain a basic N reducing adsorbent 118. Again, a basic N reducing adsorbent may be the only adsorbent used; alternatively, a basic N reducing adsorbent may be one of a plurality of adsorbents used. If a plurality of adsorbents is used, the adsorbents may be used sequentially. In such embodiments, a basic N reducing adsorbent may be used at any position in the sequence.

In the particular exemplary embodiment in FIG. 2, the purified acetonitrile stream 114 is contacted with a basic N reducing adsorbent 118, resulting in purified acetonitrile stream 120 that comprises an amount of basic N-containing compound impurities that is reduced relative to acetonitrile waste stream 102. Purified acetonitrile stream 120 may be collected for use or subjected to further purification as desired.

In some embodiments, a basic N adsorbent may comprise an acidic cation exchange resin. In such embodiments, the relative proportion of adsorbents used per volume of the acetonitrile stream to be purified (e.g., condensed overhead fraction 109 or purified acetonitrile stream 114) may vary depending on the specific adsorbent, amount of basic N-containing impurities contained in the acetonitrile stream, and desired level of basic N-containing impurities in the resulting purified acetonitrile stream. In some embodiments, an acidic cation exchange resin such as Amberlyst™-15 is used to reduce basic N-containing impurities in an acetonitrile stream at a ratio of at least about 1 g adsorbent to 10 L acetonitrile stream, such as at least about 1g adsorbent to 0.1 L acetonitrile stream.

Thus, in some embodiments the methods provided herein are used to purify an acetonitrile waste stream 102 comprising one or more basic N-containing compounds as impurities. In some embodiments, a purified acetonitrile stream 120 is generated by removing such impurities from an acetonitrile stream such that the resulting purified acetonitrile stream comprises about 100 ppm of basic N-containing compounds or less, such as about 50 ppm of basic N-containing compounds or less, such as about 25 ppm of basic N-containing compounds or less, such as about 10 ppm of basic N-containing compounds or less. In some embodiments, a purified acetonitrile stream 120 is generated by removing such impurities from an acetonitrile stream such that the resulting purified acetonitrile stream comprises from about 1 ppm to about 100 ppm of basic N-containing compounds, such as from about 1 ppm to about 50 ppm of basic N-containing compounds, such as from about 1 ppm to about 25 ppm of basic N-containing compounds, such as from about 1 ppm to about 10 ppm of basic N-containing compounds.

In some embodiments, an acid exchange resin may also reduce the amount of cations present in the purified acetonitrile stream 114. For example, impurities such as cationic Fe, Mg, Cr, Ni, Ag, and $I_2$, may be reduced by contact with a cation exchange resin. In some embodiments, cation reduction occurs concurrently with basic N reduction via contact with a basic N reducing adsorbent comprising an acidic cation exchange resin as described above. In some embodiments, the purified acetonitrile 120 comprises less than about 5 ppm cationic Fe, such as about 0.1 ppm to about 5 ppm, as an impurity. In some embodiments, the purified acetonitrile 120 comprises less than about 5 ppm cationic Mg, such as about 0.1 ppm to about 5 ppm, as an impurity. In some embodiments, the purified acetonitrile 120 comprises less than about 5 ppm cationic Cr, such as from about 0.1 ppm to about 5 ppm, as an impurity. In some embodiments, the purified acetonitrile 120 comprises less than about 5 ppm cationic Ni, such as from about 0.1 ppm to about 5 ppm, as an impurity. In some embodiments, the purified acetonitrile 120 comprises less than about 5 ppm cationic Ag, such as from about 0.1 ppm to about 5 ppm, as an impurity. In some embodiments, the purified acetonitrile 120 comprises less than about 5 ppm iodine/iodide, such as from about 0.1 ppm to about 5 ppm, as an impurity.

It may be desirable to reduce the amount of water present in the condensed purified acetonitrile 120. In some embodiments, including the example shown in FIG. 2, the purified acetonitrile 120 passes to a third adsorbent column 122. In these embodiments, the third adsorbent column 122 is configured to contain a water-reducing adsorbent (i.e., a desiccant) 124. The purified acetonitrile 120 is contacted with the water reducing adsorbent 124 to produce a purified acetonitrile 126 that exits the adsorption zone 130.

In some embodiments, potassium (K)-exchanged Linde Type A (LTA)-type molecular sieves bound with an inorganic binder may be used as a water removal adsorbent 124. It has surprisingly been found that porous desiccants exhibit increased performance (i.e., higher water adsorption capacity) for reduction of water in acetonitrile waste streams if they have been treated to partially close their pore structure. Thus, in some embodiments, one or more porous desiccants (including one or more K-exchanged LTA-type molecular sieves bound with inorganic binders) may be treated by any suitable process as known in the art to partially close the pores of the desiccant prior to use. However, care must be taken not to close the pores too much and thus restrict water adsorption capacity. The degree of pore closure may be measured by determining the smallest molecule that will not adsorb more than 1 wt. % of the molecule when exposed at one atmosphere partial pressure, also known as a plug-gauge molecule. In some embodiments, the desiccant is an LTA-type adsorbent that has been treated with steam to partially close the desiccant's pore structure to the point that the desiccant has a limited ability to adsorb ethylene, difluoromethane, or both.

In embodiments utilizing one or more LTA-type adsorbents to reduce water in a purified acetonitrile 120 from pooled acetonitrile waste from oligonucleotide synthesis, the adsorbent(s) may be used at a weight ratio of at least about 5 to about 10 mg desiccant per gram of acetonitrile to be purified. In some embodiments, one or more LTA-type adsorbents are used with a minimum water adsorption capacity of 10 wt. %. Contact may be conducted via a batch or a continuous process, with suitable apparatus, temperatures, pressures, and flow rates.

In some embodiments, reducing the amount of water present in the condensed purified acetonitrile 120 is conducted via a liquid phase process. In these embodiments, the purified acetonitrile 120 is in a liquid phase when it is contacted with the water-reducing adsorbent 124.

Thus, in some embodiments the methods provided herein are used to purify an acetonitrile waste stream 102 comprising water as an impurity. In some related embodiments, the acetonitrile waste stream 102 is fractionated and the overhead fraction is contacted with a desiccant with a partially closed pore structure. In some embodiments, the purified acetonitrile 126 that has been purified by contact with a desiccant comprises about 2000 ppm of water or less, such as about 1000 ppm of water or less, such as about 500 ppm of water or less, such as about 150 ppm of water or less, 100 ppm of water or less, such as about 50 ppm of water or less, such as about 25 ppm of water or less.

While the various embodiments above describe the acetonitrile waste stream passing from a fractionation column, then sequentially through an iodine-reducing adsorbent, through a basic N-containing compound-reducing adsorbent, and through a water-reducing adsorbent, it will be appreciated that the scope herein is not so limited. Rather, it will be understood that only one or two of the adsorbents can be used in addition to the fractionation column or that the adsorbents can be used in a different order, without limit For example, after fractionation and condensation, the condensed overhead fraction 109 can be contacted with the basic N-containing compound-reducing adsorbent and the resulting acetonitrile stream contacted with the water-reducing adsorbent, or the condensed overhead fraction 109 can be contacted with a water-reducing adsorbent and the resulting stream contacted with the iodine-reducing adsorbent.

In some embodiments, the methods provided herein are used to purify an acetonitrile waste stream 102 from oligonucleotide synthesis to generate a purified acetonitrile 126 suitable for reuse in various industrial or manufacturing processes. In some embodiments, the purified acetonitrile 126 is suitable for reuse as a between-step wash solution in an oligonucleotide synthesis conducted with between-step acetonitrile washes. In some embodiments, the purified acetonitrile 126 is greater than about 70% pure, such as greater than or equal to about 95% pure, as determined by gas chromatography.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A method for processing an acetonitrile waste stream, the method comprising the steps of:
   providing an acetonitrile waste stream containing acetonitrile, toluene, acetic acid, propanenitrile, organic and/or inorganic iodine-containing compounds, and organic and/or inorganic sulfur-containing compounds;
   fractionating the acetonitrile waste stream to produce a single overhead fraction comprising the pyridine, organic and/or inorganic iodine-containing compounds, organic and/or inorganic sulfur-containing compounds, and from about 75% to about 100% of the acetonitrile contained in the acetonitrile waste stream;
   condensing the single overhead fraction to produce a condensed single overhead fraction;
   contacting the condensed single overhead fraction with a silver-exchange zeolite to remove the organic and/or inorganic iodine-containing compounds; and
   contacting the condensed single overhead fraction with a basic anion exchange resin to remove the organic and/or inorganic sulfur-containing compounds.

2. The method of claim 1, wherein the single overhead fraction comprises a distillate from initial boiling of the acetonitrile waste stream to about 82° C. at standard pressure.

3. The method of claim 1, wherein the acetonitrile stream comprises pyridine, and wherein the method further comprises contacting the acetonitrile stream with an acidic cation exchange resin to remove the pyridine.

4. The method of claim 1, wherein the acetonitrile waste stream comprises water as an impurity, and wherein the method further comprises contacting the single overhead fraction with a desiccant to remove the water.

5. The method of claim 4, wherein the desiccant is a porous desiccant with a partially closed pore structure.

6. The method of claim 4, wherein the desiccant is a potassium-exchanged Linde Type A (LTA)-type molecular sieve bound to an inorganic binder.

7. The method of claim 4, wherein the dehydrated stream comprises less than about 150 ppm water.

8. The method of claim 1, the method further comprising heating the single overhead fraction, and reducing water in the heated single overhead fraction via vapor phase pressure-swing adsorption prior to condensing the single overhead fraction.

9. The method of claim 1, wherein the acetonitrile stream comprises water as an impurity, and wherein the method further comprises contacting the acetonitrile stream with a desiccant to produce a dehydrated stream that comprises an amount of water that is reduced relative to the acetonitrile stream.

10. The method of claim 9, wherein the desiccant is a porous desiccant with a partially closed pore structure.

11. The method of claim 9, wherein the desiccant is a potassium-exchanged Linde Type A (LTA)-type molecular sieve bound to an inorganic binder.

12. The method of claim 9, wherein the dehydrated stream comprises less than about 150 ppm water.

* * * * *

UNITED STATES PATENT AND TRADEMARK OFFICE
CERTIFICATE OF CORRECTION

PATENT NO. : 10,336,690 B2  
APPLICATION NO. : 14/608911  
DATED : July 2, 2019  
INVENTOR(S) : Gregory J. Gajda et al.

Page 1 of 1

It is certified that error appears in the above-identified patent and that said Letters Patent is hereby corrected as shown below:

In the Claims

Column 16, Claim 1, Lines 8-9; replace "the pyridine, organic" with --any pyridine, if present, and the organic--

Signed and Sealed this
Nineteenth Day of January, 2021

Andrei Iancu
*Director of the United States Patent and Trademark Office*